United States Patent [19]

Maurer et al.

[11] Patent Number: 5,887,778
[45] Date of Patent: Mar. 30, 1999

[54] METHOD OF AND APPARATUS FOR WELDING SURGICAL NEEDLE STOCK TO A METAL TAPE

[75] Inventors: Thomas D. Maurer, San Angelo, Tex.; Michael J. Brown, deceased, late of San Angelo, Tex., by Mary Brown, administratrix

[73] Assignee: Ethicon, Inc., New Brunswick, N.J.

[21] Appl. No.: 788,857

[22] Filed: Jan. 23, 1997

[51] Int. Cl.$^6$ ................................................. B23K 37/04
[52] U.S. Cl. ........................ 228/212; 228/6.1; 228/49.1
[58] Field of Search ................................. 228/6.1, 49.1, 228/182, 212

[56] References Cited

U.S. PATENT DOCUMENTS

| | | | |
|---|---|---|---|
| 2,326,022 | 8/1943 | Everett | 228/182 |
| 3,684,474 | 8/1972 | Chisholm | 228/182 |
| 4,359,623 | 11/1982 | Fanning | 228/6.1 |

FOREIGN PATENT DOCUMENTS 516028  12/1939  United Kingdom ................... 228/212

*Primary Examiner*—Patrick Ryan
*Assistant Examiner*—Jeffrey T. Knapp
*Attorney, Agent, or Firm*—Thompson & Knight

[57] ABSTRACT

A method and apparatus is available for receiving surgical needle stock from a needle fabrication line and welding the surgical needle stock to a metal tape. The apparatus includes a welding station where the needle stock is welded to the tape. A tape indexing unit is arranged to move the metal tape through the welding station. A preload chuck is arranged to receive the surgical needle stock from the needle fabrication line and a gripper assembly is arranged to receive the surgical needle stock from the preload chuck and transfer the surgical needle stock from the preload chuck to the welding station.

36 Claims, 7 Drawing Sheets

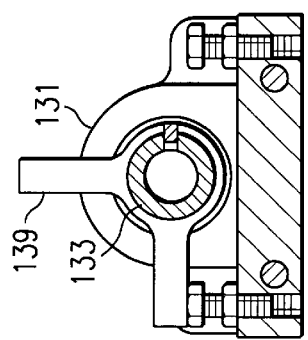
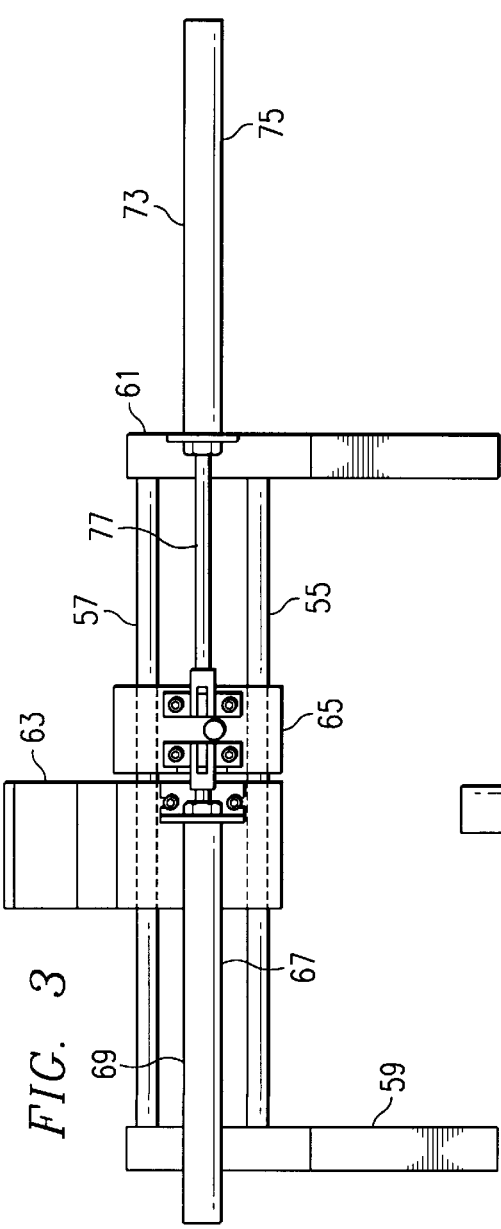
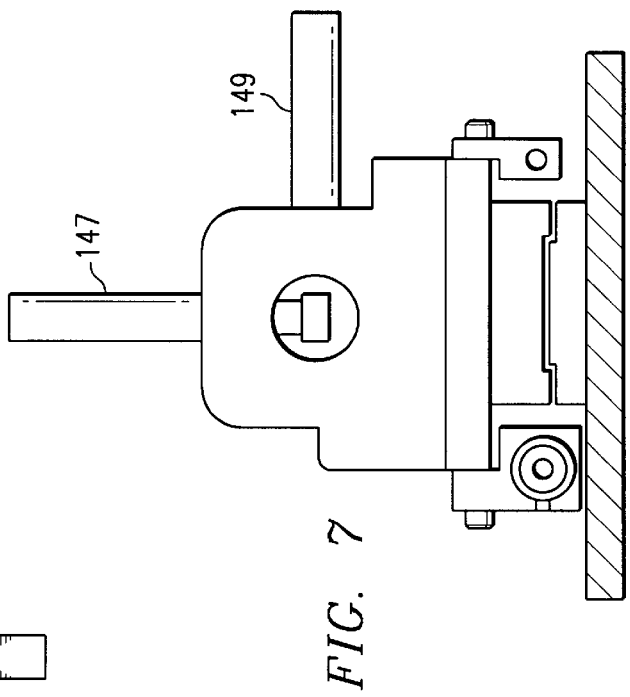

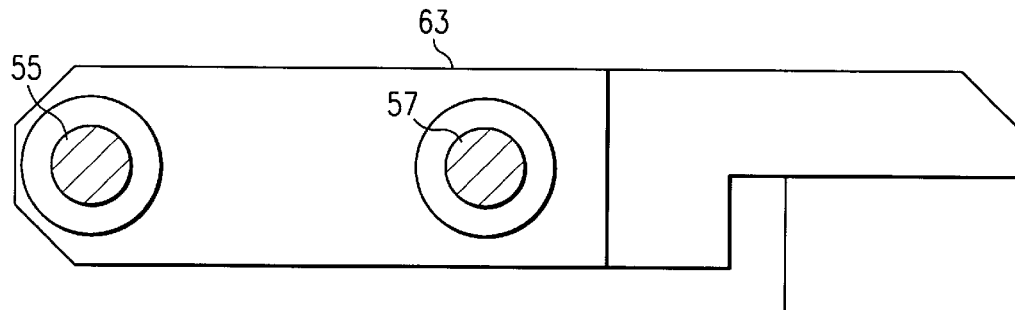
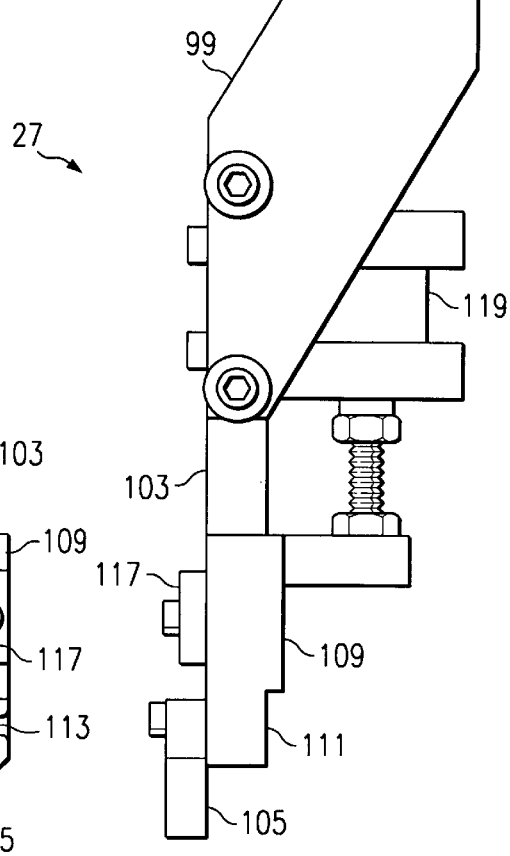
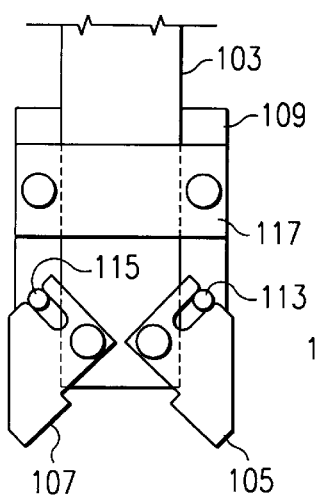
FIG. 9
FIG. 10B    FIG. 10A

METHOD OF AND APPARATUS FOR WELDING SURGICAL NEEDLE STOCK TO A METAL TAPE

FIELD OF THE INVENTION

The present invention relates generally to automated article handling and manufacturing apparatus and methods, and more particularly to a method of and apparatus for welding surgical needle stock to a metal tape.

DESCRIPTION OF THE PRIOR ART

There is a tremendous demand for surgical needles. Accordingly, the industry constantly seeks to increase its production volume. However, surgical needles are relatively small in size and made of very hard materials. Additionally, there is a substantial amount of hand work involved in manufacturing surgical needles. Therefore, it is difficult to produce surgical needles in high volumes and still meet the exacting quality standards required for medical products.

Surgical needles are typically sold as needle and suture units. There are generally two types of needles. One type is the drilled needle, in which the suture is swaged into a small hole drilled axially into the end of the needle. The other type is the channel, in which a channel is formed in the needle stock during manufacture and the suture is attached to the needle by crimping or otherwise closing the channel around the end of the suture.

Surgical needles are made from what is essentially wire. The wire is cut into lengths and the lengths are straightened. Then, steps are performed to form the needle point and the channel or axial hole, and to curve the needle. The foregoing steps have generally been automated by means of a line of machines. The needle stock is passed from one machine to the next on a transfer bar or the like.

After the needle stock has been pointed, curved, and drilled or channeled, there is a substantial amount of additional processing required to make a finished needle. Among other things, the needles must be electropolished, siliconized, annealed, and sterilized. Currently, substantial hand work is involved in the post-machining manufacturing processes. For example, after the needle stock is received from the machines, it must be manually hung on a carrier for transport through electropolishing and siliconizing. Accordingly, some of the advantages in speed and efficiency achieved by automating the machining processes are negated or limited by the manual labor involved in the post machining process steps.

Accordingly, it is an object of the present invention to automate further the manufacture of surgical needles.

SUMMARY OF THE INVENTION

Briefly stated, the present invention provides a method and apparatus for receiving surgical needle stock from a line of needle fabrication machines and welding the surgical needle stock to a metal tape. The needle stock may then be transported on the metal tape through post-machining processing steps such as electropolishing, siliconizing, resistance annealing, sterilizing and the like.

The apparatus includes a welding station where the needle stock is welded to the tape. A tape indexing unit is arranged to move the metal tape through the welding station. A preload chuck is arranged to receive the surgical needle stock from the needle fabrication line and a gripper assembly is arranged to transfer the surgical needle stock from the preload chuck to the welding station.

The welding station includes a pair of normally spaced apart plates that are adapted to clamp the needle stock into engagement with the tape, and a welding rod that is arranged to weld the needle stock to the tape. One of the plates has a welding rod hole for the passage of the rod therethrough into contact with the needle stock and the tape.

The preload chuck includes a housing and a spindle that is rotatably mounted in the housing. The spindle includes a fixed jaw and a movable jaw pivotally mounted to the spindle. The movable jaw is engageable with the fixed jaw to grip a needle stock therebetween and a spring or the like is positioned to urge the movable jaw toward a normally closed position. A mechanism is provided for rotating the spindle between a first angular position with respect to the housing and a second angular position with respect to the housing. A first actuator is arranged to move the movable jaw to an open position when the spindle is in the first angular position, and a second actuator is arranged to move the movable jaw to an open position when the spindle is in the second angular position. When the spindle is between the first and second angular positions, the spring keeps the jaws closed. An actuator moves the housing axially between a first axial position, in which the jaws receive the needle stock, and a second axial position, in which needle stock is transferred to the gripper assembly.

The gripper assembly includes a carriage that is slidingly mounted on rails to be translatable between a first position that is adjacent the preload chuck and a second position that is adjacent the welding station. The carriage carries a gripper support that has a pair of gripper jaws pivotally mounted thereto. The gripper jaws are movable between an open, receiving and releasing, position and a closed, gripping, position.

The rails are supported between a pair of spaced apart rail supports. A block is slidingly mounted to the rails between the carriage and one of the supports. A first actuator is connected between the block and one of said rail supports and a second actuator is connected between the carriage and the block. The first and second actuators cooperate to move the carriage back and forth on the rails between the first and second positions.

The metal tape is fed to the tape indexing unit from a supply reel. The metal tape with the needle stock welded thereto is taken-up on a take-up reel. The apparatus includes a metal foil reel the supplies metal foil to the take-up reel to be wound up with the metal tape. The metal foil serves to space apart the layers of needle stock welded to the metal tape. The supply reel and the take-up reel are driven independently by respective motors. A controller operates the motor of the take-up reel responsive to detection of slack in the metal tape between the tape indexing unit and the take-up reel. A controller operates the motor of the supply reel responsive to tension in the metal tape between the supply reel and the tape indexing unit.

BRIEF DESCRIPTION OF THE DRAWINGS

FIG. 3 is a top view showing details of the gripper assembly.

FIG. 7 is a view taken along line 7—7 of FIG. 5.

FIG. 8 is a view taken along line 8—8 of FIG. 5.

FIG. 9 is a side view of the gripper assembly of the present invention.

FIGS. 10A and 10B are partial front views showing details of the gripper assembly of the present invention.

DESCRIPTION OF THE PREFERRED EMBODIMENT

Figure 1:
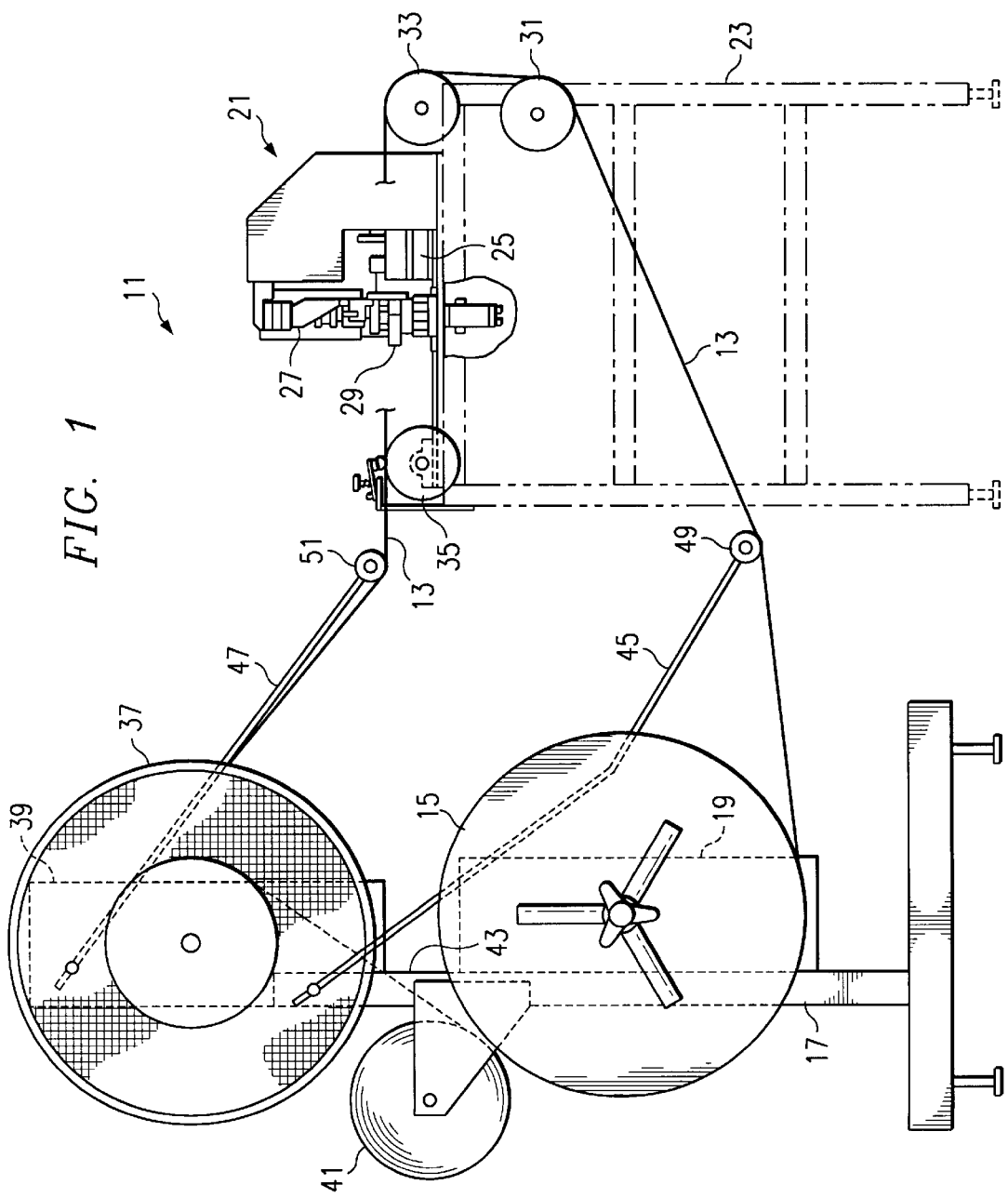
FIG. 1 is a side view of the apparatus of the present invention.

Referring now to the drawings, and first to FIG. 1, the apparatus of the present invention is designated generally by the numeral 11. Apparatus 11 is adapted to receive surgical needle stock from a line of needle fabrication machines and weld the surgical needle stock to a metal tape 13. Metal tape 13 is supplied to machine 11 on a supply reel 15. Supply reel 15 is supported by a stand 17 and it is driven to rotate on its axis by a suitable motor and control unit, shown generally at 19.

The surgical needle stock is transferred from the fabrication line and welded to tape 13 at a transfer and welding area designated generally by the numeral 21. Transfer and welding area 21 is supported by a base, indicated generally at 23, and it includes a tape indexing unit 25, a gripper assembly 27, and a welding station 29. Transfer and welding area 21 also includes a preload chuck which is not shown in FIG. 1 but which is shown generally in FIG. 2, and in detail in FIGS. 5–8.

In the preferred embodiment, tape indexing unit 25 is a Rapid Air model A2-E unit. Tape indexing unit 25 pulls tape 13, which is trained around pulleys 31 and 33 rotatably mounted to stand 23, from supply reel 15 and effectively pushes tape 13 through welding station 29. Tape 13 is of sufficient stiffness so that it may be pushed through welding station and over a pulley 35 rotatably mounted to stand 23 to a take-up reel 37.

Take-up reel 37 is supported by stand 17 and it is driven to rotate by means of a suitable motor and controller, shown generally at 39. The sides of take-up reel 37 are preferably perforated so that various processing steps, such as sterilization, may be performed on the needle stock and tape as it is wound on take-up reel 37.

Apparatus 11 also includes a foil supply reel 41 that is rotatably mounted to stand 17. Foil supply reel 41 carries metal foil 43 that is arranged to be wound onto take-up reel 37 along with metal tape 13. Metal foil 43 separates adjacent layers of needles wound onto take-up reel 37.

Motor and controller combinations 19 and 39 are operated by operator arms 45 and 47, respectively; Operator arm 45 is pivotally mounted to stand 17 and it includes a roller 49 in contact with tape 13. Operator arm 45 effectively senses tension in tape 13 between supply reel 15 and pulley 31. As tension increases, tape 13 straightens between supply reel 15 and pulley 31 and rotates operator arm 45 counterclockwise. At a predetermined point in its counterclockwise rotation, operator arm 45 actuates motor and controller 19 to drive supply reel 15 to pay out tape 13. As tape 13 is paid out, operator arm 45 rotates counterclockwise until it reaches a predetermined point that turns off motor 19.

Operator arm 47 is pivotally mounted to stand 17 and includes a roller 51 in contact with tape 13. Operator arm 47 effectively senses slack in tape 13. Thus, as tape 13 is advanced toward take-up reel 37, operator arm 47 is allowed to rotate clockwise. At a predetermined point in its clockwise rotation, operator arm 47 actuates motor and controller 39 to drive take-up reel 37 to take up slack in tape 13, which rotates operator 47 counterclockwise. At a predetermined point in its clockwise rotation, operator arm 47 turns off motor 39.

Thus, reels 15 and 37 are driven independently of each other to compensate for changing tape radii as tape 13 is moved from supply reel 15 to take-up reel 37. Tape 14 is moved between reels 15 and 37 at a constant linear speed set by tape indexing unit 25.

Figure 2:
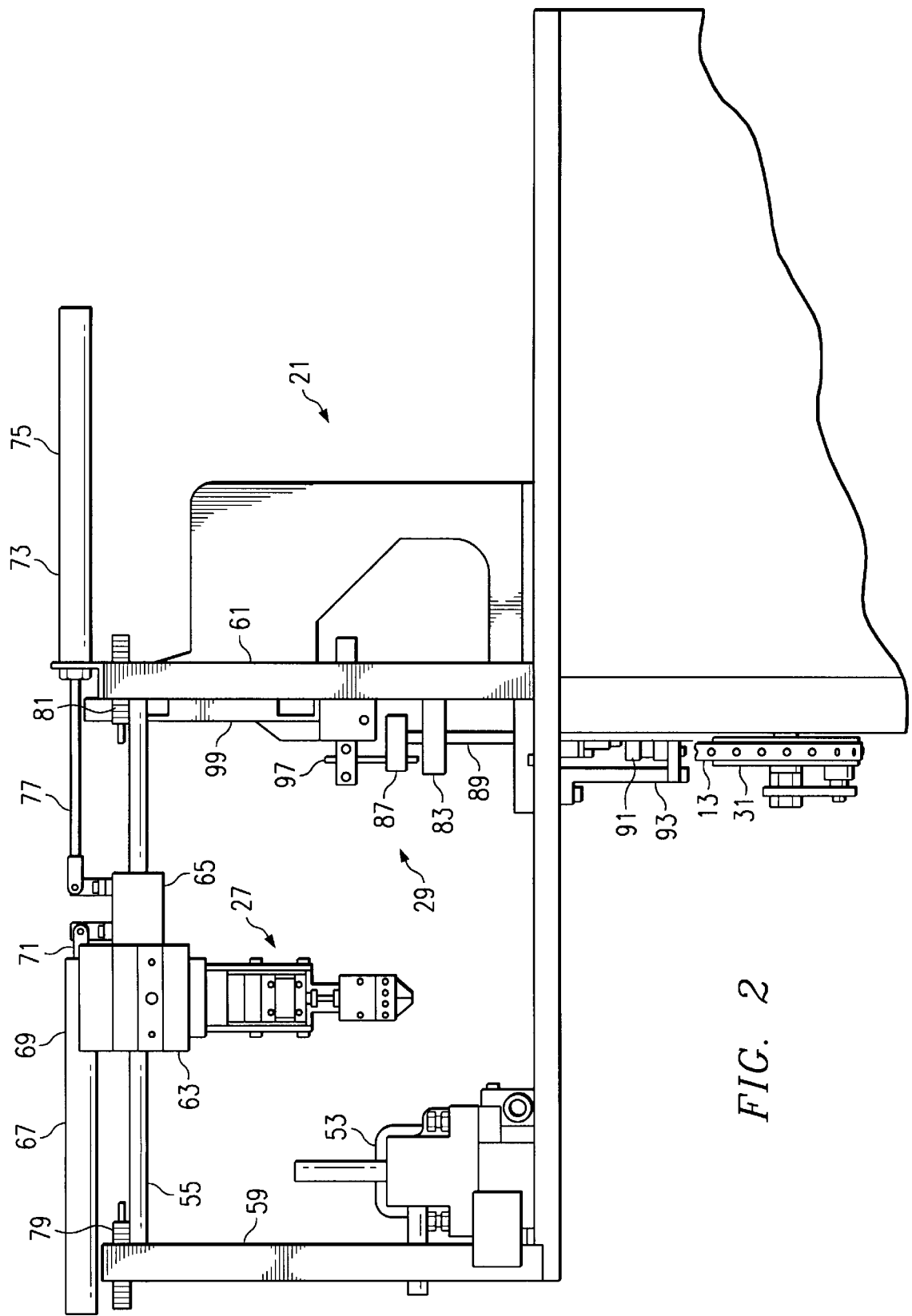
FIG. 2 is a front view showing details of the preload chuck, gripper assembly, and welding station of the present invention.

Referring now to FIG. 2, there is shown additional details of the transfer and welding area 21 of the present invention. As shown in FIGS. 2 and 3, gripper assembly 27 is moveable back and forth between a preload chuck 53 and welding station 29 on a pair of spaced apart rails 55 and 57. Rails 55 and 57 are supported by spaced apart rail supports 59 and 61. Gripper assembly 27 includes a carriage 63 slidingly supported on rails 55 and 57. Gripper assembly 27 also includes a block 65 slidingly mounted on rails 55 and 57 between carriage 63 and rail support 61. A pneumatic linear actuator 67 that includes a cylinder 69 that is connected to carriage 63 and a piston rod 71 that is connected to block 65. Thus, when pneumatic actuator 67 is extended, carriage 63 and block 65 are urged apart from each other.

A second pneumatic actuator 73 is connected between block 65 and rail support 63. Pneumatic actuator 71 includes a cylinder 75 that is connected to rail support 61 and a piston rod 77 that is connected to block 65. Thus, when pneumatic actuator 73 is extended, block 65 is urged on rails 55 and 57 toward rail support 59.

From the foregoing, it may be seen that pneumatic actuators 67 and 73 cooperate to translate gripper assembly 27 back and forth between preload chuck 53 and welding station 29. In FIGS. 2 and 3, carriage 63 is shown about midway between preload chuck 53 and welding station 29 with actuator 73 extended and actuator 27 contracted. When both actuators 65 and 73 are extended, gripper assembly is in the vicinity of preload chuck 53. Conversely, when actuators 67 and 73 are both retracted, gripper assembly 27 is in the vicinity of welding station 29. Shock absorbing stops 79 and 81 are threadedly engaged with rail supports 59 and 61 respectively. Stops 79 and 81 are positionable to locate gripper assembly 27 precisely with preload chuck 53 and welding station 29.

Figure 4:
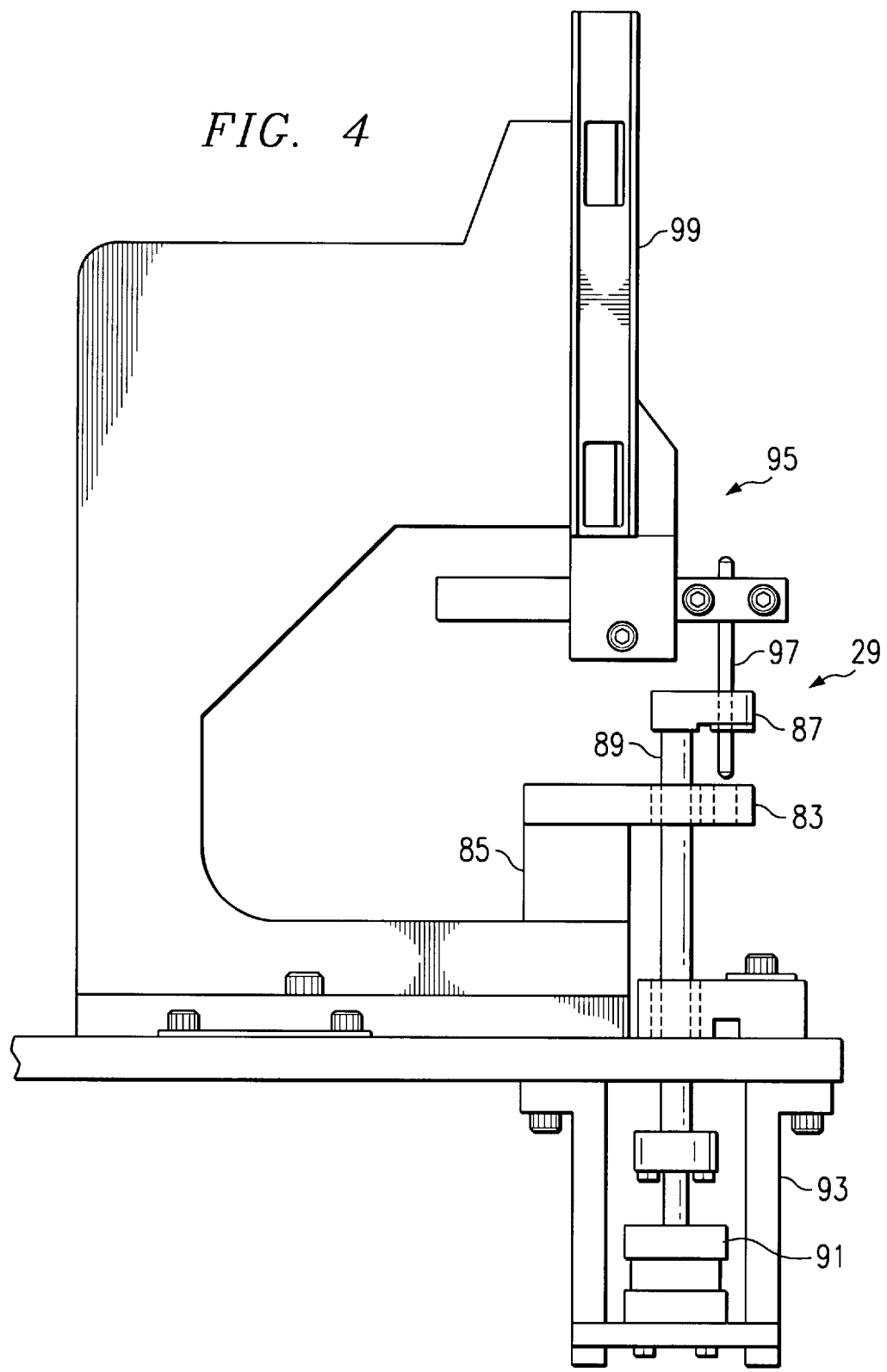
FIG. 4 is a side view of the welding station of the present invention.

As shown in FIGS. 2 and 4, welding station 29 includes a fixed plate 83 immovably supported on a support block 85 and a moveable plate 87 movably mounted with respect to fixed plate 87 on an operator rod 89. Operator rod is actually moveable with respect to fixed plate 83 by means of a pneumatic cylinder 91 supported by a support bracket 93. Pneumatic cylinder 91 is preferably a Bimba cylinder and is adapted to move moveable plate 87 into clamping engagement with fixed plate 83 with the metal tape and needle stock (neither shown in FIGS. 2 and 4) therebetween.

Welding station 29 also includes a welding head assembly 95, which in the preferred embodiment is a Aidlin Automation Model No. TW-3A0 weld head assembly. Weld head assembly 95 includes a welding rod 97 that passes through a hole in moveable plate 87. The tip of welding rod 87 is positioned above fixed plate 83. Welding head assembly 95 includes an actuator 99 that is adapted to move welding rod 97 axially downwardly into contact with a needle stock clamped to the metal tape between fixed plate 83 and moveable plate 87. Preferably, welding head assembly 95 includes a pressure sensor (not shown) that actuates the welding current when the tip of rod 97 is in appropriate contact with a needle. Also, welding station 29 preferably includes an optical sensor that determines when a needle is positioned between fixed plate and moveable plate 87.

Referring now to FIGS. 9 and 10A–10B, there is shown additional details of gripper assembly 27. Carriage 63 is shown slidingly supported on rails 55 and 57 on appropriate bushings. Carriage 63 carries a gripper arm 99 that is rotatably attached to carriage 63 with a ninety-degree rotating device 101. In the preferred embodiment, rotating device 101 is a Barrington Automation model RD1 and it is adapted to rotate gripper arm 99 ninety degrees between a first position, as shown in FIG. 9 to receive a needle stock from preload chuck 53 of FIG. 2, and a second position, as shown generally in FIGS. 10A and 10B to transfer the needle stock to welding station 29 of FIG. 2.

Gripper arm 99 includes a gripper support 103. Gripper support 103 extends axially downwardly from gripper arm 99 and it includes a pair of gripper jaws 105 and 107 pivotally mounted thereto. Gripper jaws 105 and 107 are moveable between and closed position, as shown in FIG. 10A, and an opened position, as shown in FIG. 10B, by means of an operator 109 axially slidingly mounted on gripper support 103. Operator 109 includes a body 111 that carries of pair of spaced apart pins 113 and 115 that engage slots in gripper jaws 105 and 107, respectively. Body 111 of operator 109 is held in engagement with gripper support 103 by means of a keeper 117.

Operator 109 is axially moveable on gripper support 103 by means of a pneumatic cylinder 119. In the preferred embodiment, pneumatic cylinder 119 is manufactured by Bimba. In the position of FIG. 10A, operator 109 is extended and pins 113 and 115 hold jaws 105 and 107 in engagement with each other. In the position of FIG. 10B, in which operator 109 is retracted, jaws 105 are opened by the action of pins 113 and 115.

Figure 5:
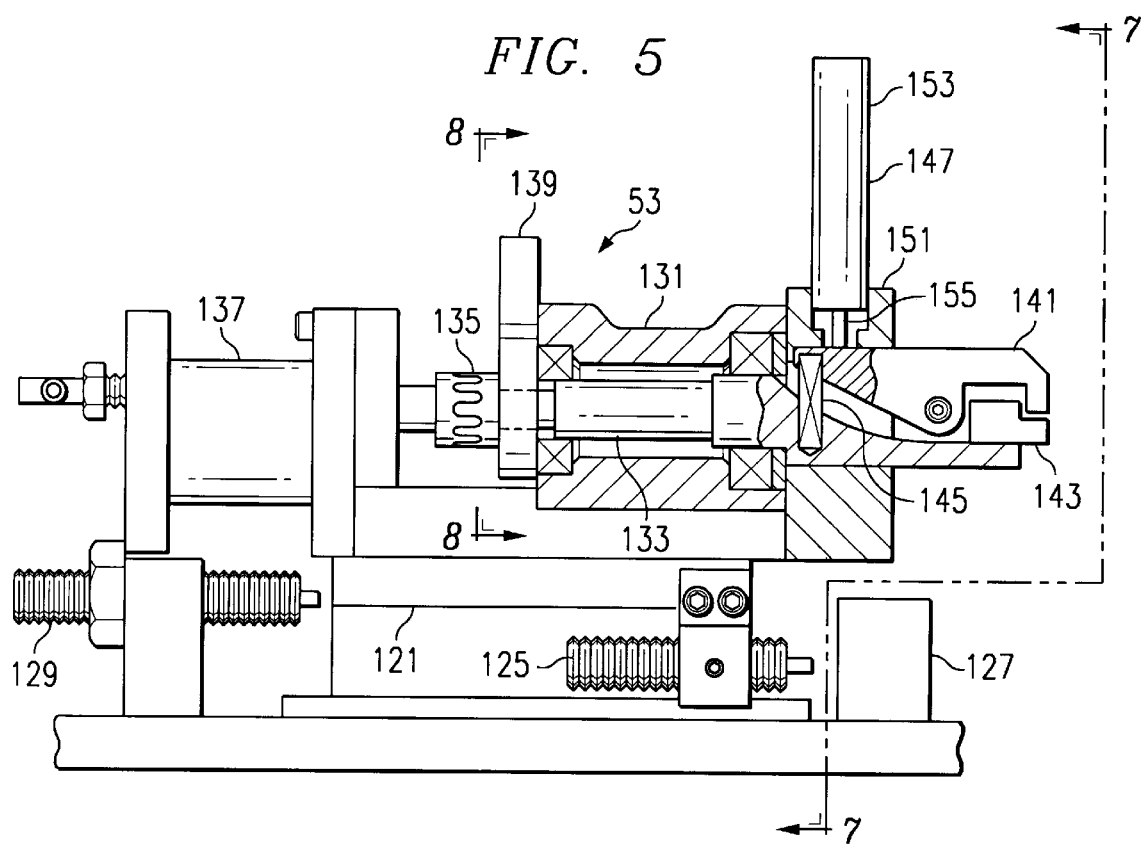
FIG. 5 is a side partial section view of the preload chuck of the present invention.
Figure 6:
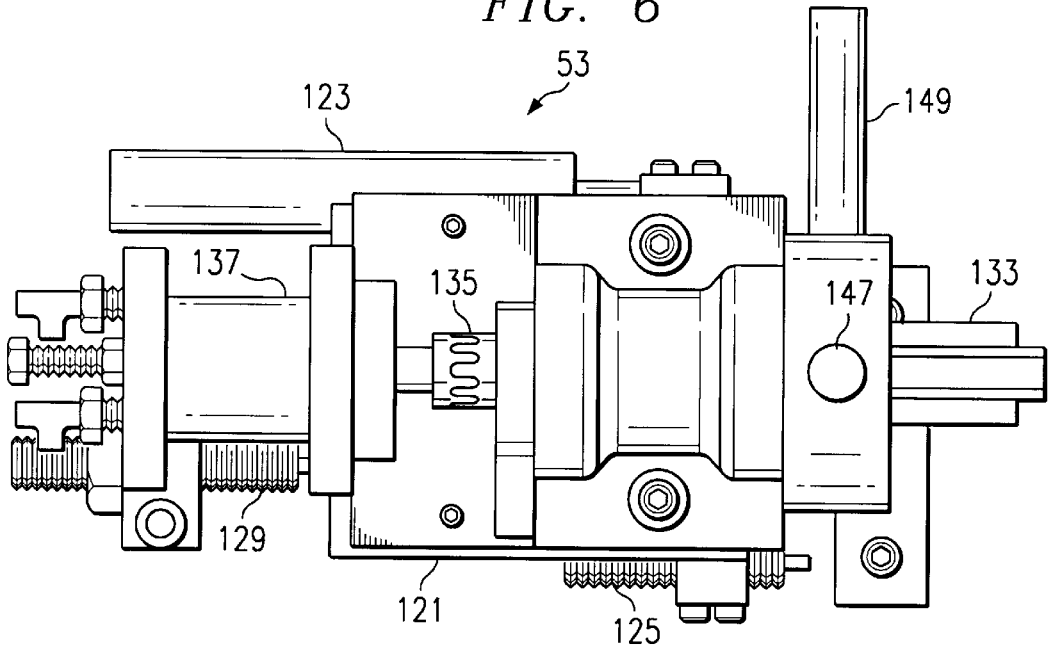
FIG. 6 is a top view of the preload chuck of the present invention.

Referring now to FIGS. 5 and 6, the preload chuck of the present invention is designated generally by the numeral 53. Preload chuck 53 is adapted to receive needle stock from a needle fabrication line and transfer the stock to gripper assembly 27. Preload chuck 53 is supported on a carriage 121 for movement by means of a pneumatic actuator 123 between a first axial position to receive the needle stock, and a second axial position to transfer the needle stock to the gripper assembly. A shock absorbing stop 125 is carried by carriage 21 and it is engageable with a block 127 to limit the forward travel of carriage 121. A shock absorbing stop 129 is positioned to limit the forward travel of carriage 121. Shock absorbing stops 125 and 129 are of the same type as stops 79 and 81 of FIG. 2, which limit the travel of gripper assembly on rails 55 and 57.

Preload chuck 53 includes a generally cylindrical housing 131 mounted to carriage 121 and a spindle 133 rotatably mounted within housing 131 on suitable bearings. Spindle 133 is coupled by means of a suitable coupler 135 to a rotating device 137, which in the preferred embodiment is a Rotac Pneumatic Actuator Model LP-11-1V. As best shown in FIG. 8, a ninety-degree rotating stop 139 is keyed to spindle 133. Thus, spindle 133 is rotatable back and forth ninety degrees with respect to housing 31 between a first position and a second position.

Spindle 133 carries a moveable jaw 141 and a fixed jaw 143. Moveable jaw 141 is pivotally mounted in spindle 133 and a spring 145 is provided for normally urging jaws 141 and 143 into engagement with each other. Thus, jaws 141 and 143 are normally held closed to grip a surgical needle by the action of spring 145. In order to open jaws 141 and 143 to grab or release a needle stock, preload chuck 55 includes a pair of pneumatic actuators 147 and 149. Pneumatic actuators 147 and 149 are carried by a collar 151 connected to housing 131. As shown in FIG. 5, actuator 147 includes a cylinder 153 and a piston rod 155. Piston rod 155 is engageable with moveable jaw 141 when spindle is in the position in FIG. 5, thereby to open jaws 141 and 143. Similarly, when spindle 133 is rotated to its second angular position (not shown) a similar piston rod in actuator 149 engages moveable jaw 141 to open jaws 141 and 143. When spindle 133 is in an angular position between its first and second ninety-degree spaced apart positions, jaws 141 and 143 are urged into engagement with each other by spring 145.

Figure 11:
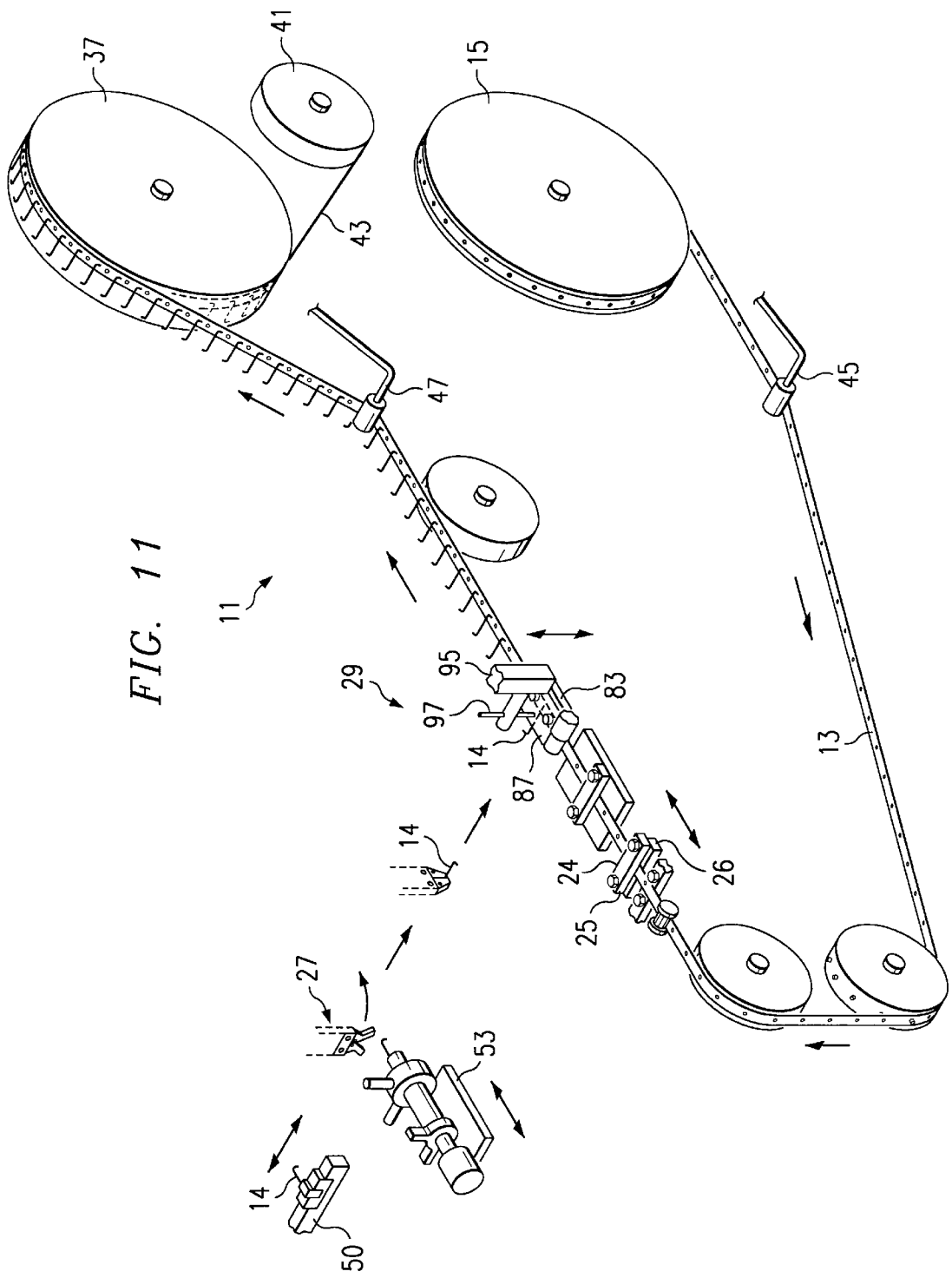
FIG. 11 is a pictorial view illustrating the operation of the apparatus and method of the present invention.

The operation of the apparatus and method of the present invention may be best understood with reference to FIG. 11. Metal tape 13 runs between supply reel 15 and take-up reel 37. Reels 15 and 37 are driven by motors (not shown in FIG. 11) that are operated by operator arms 45 and 47 respectively. Foil reel 41 is positioned to supply foil 43 to take-up reel 37. Foil 42 spaces apart adjacent layers of needles wound onto takeup reel 37.

Tape 13 is moved stepwise through welding station 29 by tape indexing unit 25. As shown in FIG. 11, tape 13 includes linearly spaced apart perforations. Tape indexing unit 25 includes an upper plate 24 and a lower plate 26. One of plates 24 and 26 includes a pin that engages a perforation in tape 13. Tape indexing unit 25 includes actuators that move plates 24 and 26 into and out of engagement with a perforation in tape 13 and other actuators that move plates 24 and 26 together back and forth to move tape 13 through welding station 29. Tape indexing unit 25 is preferably a commercially available Rapid Air model A2-E unit.

Welding station 29 includes a fixed lower plate 83 and a moveable upper plate 87 between which passes metal tape 13. Plates 83 and 87 are moveable with respect to each other to clamp therebetween tape 13 and a needle stock 14. Welding station 29 includes a welding head 95 that includes a welding rod 97. Welding rod 97 is moveable through a hole in moveable upper plate 87 to weld needle 14 to tape 13.

Needle stock 14 is carried down a line of machines (not shown) on a transfer bar 50. Transfer bar 50 is moveable axially back and forth to transfer needle stock 14 from machine to machine. Preload chuck 53 is arranged to move axially back and forth to receive a needle stock 14 from transfer bar 50 in a first position and release the needle stock to gripper assembly 27 in its second axial position.

The needle stock is shaped somewhat like a fishhook, with a straight shank and a curved part that will separated from the shank to become the finished needle. The end of the shank opposite the curved part is bent ninety-degrees to form a tail. The tail serves to prevent the needle stock from twisting as various machining operations are performed on the needle stock. Preferably, according to the present invention, the needle stock is welded flat to tape 13. In the preferred process for machining the needle stock, the tail is oriented vertically, but in the preferred embodiment of the present invention, tape 13 passes through welding station 29 horizontally. Thus, it is necessary to rotate the shank of the needle stock ninety degrees about its axis between transfer bar 50 and welding station 29. Accordingly, spindle 133 is arranged to rotate ninety degrees between the time it receives needle stock 14 from transfer bar 50 and the time it passes needle stock 14 to gripper assembly 27.

Gripper assembly 27 includes a pair of jaws 105 and 107 that are adapted to take needle stock 14 from preload chuck 53. Gripper assembly 27 is arranged to move linearly back and forth between preload chuck 53 and welding station 29 and to rotate ninety degrees during its linear travel. Gripper assembly 27 inserts needle stock tail-first between plates 83 and 87 of welding station. When plates 83 and 87 move into clamping engagement with needle stock 14 and tape 13, the jaws of gripper assembly 27 release and gripper assembly 27 returns to preload chuck 53 to get another needle stock 14.

From the foregoing, it may be seen that the method and apparatus of the present invention substantially increase the speed and efficiency of manufacturing surgical needles. The method and apparatus of the present invention eliminates the need to handle the needles individually during post-machining processing. The needle stock is welded to a metal tape at the same rate it is received from an automated manufacturing line. Thus, the method and apparatus reduces both time and expense involved the manufacture of surgical needles. Moreover, by welding the needle stock to the metal tape, subsequent post-machining processing, such as electropolishing, siliconizing, annealing, sterilizing, and the like may be further automated to increase the overall efficiency of the needle manufacturing process.

The method and apparatus of the present invention have been illustrated and described with reference to a preferred embodiment. However, those skilled in the art will recognize that certain disclosed features and combinations of features may be used independently of or in combination with other features. Accordingly, the scope of the invention is set forth in the Claims.

What is claimed is:

1. A method of manufacturing surgical needles, which comprises the steps of:
    receiving surgical needle stock from a needle machining line; and,
    welding said surgical needle stock received from said needle machining line at linearly spaced apart points to a metal tape.

2. The method as claimed in claim 1, wherein said welding step includes the steps of:
    clamping a needle stock to a point on said metal tape;
    welding said clamped needle stock to said metal tape; and,
    indexing said metal tape.

3. The method as claimed in claim 1, including the step of winding said metal tape with said surgical needle stock welded thereto onto a take-up reel.

4. The method as claimed in claim 3, including the step of winding a strip of foil onto said take-up reel with said metal tape to space apart adjacent layers of metal tape with said surgical needle stock welded thereto.

5. Apparatus for receiving surgical needle stock from a needle fabrication line and welding said surgical needle stock to a metal tape, which comprises:
    a welding station;
    a tape indexing unit arranged to move said metal tape through said welding station;
    a preload chuck arranged to receive said surgical needle stock from said needle fabrication line;
    a first rail support positioned adjacent said preload chuck;
    a second rail support positioned adjacent said welding station;
    a pair of spaced apart parallel rails supported between said first and second rails supports;
    a carriage slidingly mounted on said rails for movement between a first position adjacent said preload chuck and a second position adjacent said welding station;
    means for translating said carriage between said first and second positions;
    a gripper support carried by said carriage;
    a pair of gripper jaws pivotally mounted to said gripper support; and,
    means for moving said gripper jaws between an open position and a closed position.

6. The apparatus as claimed in claim 5, wherein said means for translating said carriage between said first and second positions includes:
    a block slidingly mounted to said rails;
    a first actuator connected between said block and one of said rail supports; and,
    a second actuator connected between said carriage and said block.

7. The apparatus as claimed in claim 5, wherein said carriage includes means for rotating said gripper support between a first position and a second position.

8. The apparatus as claimed in claim 5, wherein each of said gripper jaws includes a slot, and said means for moving said gripper jaws between an open position and a closed position includes:
    an operator axially slidingly mounted to said gripper support, said operator including a pair of pins engaging said slots in said gripper jaws; and,
    means for moving said operator axially with respect to said gripper support, thereby to open and close said gripper jaws.

9. The apparatus as claimed in claim 5, wherein said preload chuck includes:
    a pair of chuck jaws;
    means for moving said chuck jaws between an open position and a closed position.

10. The apparatus as claimed in claim 9, including means for moving said chuck jaws axially between a first axial position to receive a needle stock from said needle fabrication line and a second axial position to transfer a needle stock to said gripper jaws.

11. Apparatus for receiving surgical needle stock from a needle fabrication line and welding said surgical needle stock to a metal tape, which comprises:
    a welding station;
    a tape indexing unit arranged to move said metal tape through said welding station;
    a preload chuck arranged to receive said surgical needle stock from said needle fabrication line; and,
    a gripper assembly arranged to transfer said surgical needle stock from said preload chuck to said welding station.

12. The apparatus as claimed in claim 11, including:
    supply reel means for supplying said metal tape to said tape indexing unit; and,
    take-up reel means for receiving said metal tape from said tape indexing unit.

13. The apparatus as claimed in claim 12, including:
    foil reel means for supplying a foil strip to said take-up reel means.

14. The apparatus as claimed in claim 11, wherein said welding station comprises:
    a first plate, said first plate having a welding rod opening therein;
    a second plate normally spaced apart from said first plate, wherein said metal tape is arranged to move between said first and second plates;

means for moving said first and second plates into clamping engagement with each other with said metal tape and said needle stock clamped therebetween; and, a welding head movably mounted with respect to said first and second plates, said welding head including a welding rod, said welding rod being movable through said welding rod opening in said first plate into engagement with said needle stock and said metal tape to weld said needle stock to said metal tape.

15. The apparatus as claimed in claim 14, wherein said welding rod opening is defined by a hole through said first plate.

16. The apparatus as claimed in claim 14, wherein said second plate is fixedly mounted and said first plate is movably mounted with respect to said second plate.

17. The apparatus as claimed in claim 11, wherein said preload chuck includes:

a housing;

a spindle rotatably mounted in said housing, said spindle including a fixed jaw;

a movable jaw pivotally mounted to said spindle, said movable jaw being engageable with the fixed jaw of the spindle to grip a needle stock therebetween;

means for urging the movable jaw toward a normally closed position;

means for rotating said spindle in said housing between a first angular position with respect to said housing and a second angular position with respect to said housing;

means for moving said movable jaw to an open position when said spindle is in said first angular position;

means for moving said movable jaw to an open position when said spindle is in said second angular position; and, means for moving said housing axially between a first axial position and a second axial position.

18. The apparatus as claimed in claim 17, wherein said means for urging the movable jaw toward a normally closed position includes a spring positioned between the spindle and the movable jaw.

19. The apparatus as claimed in claim 17, wherein said means for moving said movable jaw to an open position when said spindle is in said first angular position includes a first jaw actuator carried by said housing and engageable with said movable when said spindle is in said first position.

20. The apparatus as claimed in claim 17, wherein said means for moving said movable jaw to an open position when said spindle is in said second angular position includes a second jaw actuator carried by said housing and engageable with said movable jaw when said spindle is in said second position.

21. The apparatus as claimed in claim 17, including stop means for stopping axial movement of said housing in said first and second axial positions.

22. The apparatus as claimed in claim 11, wherein said preload chuck includes:

a fixed jaw;

a movable jaw pivotally mounted with respect to said fixed jaw, said movable jaw being engageable with said fixed jaw to grip a needle stock therebetween;

means for urging the movable jaw toward a normally closed position with respect to said fixed jaw; and, means for moving said movable jaw to an open position with respect to said fixed jaw.

23. The apparatus as claimed in claim 22, wherein said means for urging the movable jaw toward a normally closed position includes a spring positioned between the spindle and the movable jaw.

24. The apparatus as claimed in claim 22, wherein said fixed jaw is carried by spindle rotatably mounted in a housing, and said preload chuck includes:

means for rotating said spindle in said housing between a first angular position with respect to said housing and a second angular position with respect to said housing.

25. The apparatus as claimed in claim 24, wherein said means for moving said movable jaw to an open position with respect to said fixed jaw includes:

means for moving said movable jaw to an open position when said spindle is in said first angular position; and, means for moving said movable jaw to an open position when said spindle is in said second angular position.

26. The apparatus as claimed in claim 25, wherein said means for moving said movable jaw to an open position when said spindle is in said first angular position includes a first jaw actuator carried by said housing and engageable with said movable when said spindle is in said first position.

27. The apparatus as claimed in claim 25, wherein said means for moving said movable jaw to an open position when said spindle is in said second angular position includes a second jaw actuator carried by said housing and engageable with said movable jaw when said spindle is in said second position.

28. The apparatus as claimed in claim 25, including means for moving said fixed jaw and said movable jaw axially between a first axial position to receive said needle stock from said needle fabrication line and a second axial position to deliver said needle stock to said gripper assembly.

29. The apparatus as claimed in claim 11, wherein said gripper assembly includes:

a carriage translatable between a first position adjacent said preload chuck and a second position adjacent said welding station;

means for translating said carriage between said first and second positions;

a gripper support carried by said carriage;

a pair of gripper jaws pivotally mounted to said gripper support; and, means for moving said gripper jaws between an open position and a closed position.

30. The apparatus as claimed in claim 29, including means for rotating said gripper support between a first position and a second position.

31. The apparatus as claimed in claim 29, wherein each of said gripper jaws includes a slot, and said means for moving said gripper jaws between an open position and a closed position includes:

an operator axially slidingly mounted to said gripper support, said operator including a pair of pins engaging said slots in said gripper jaws; and, means for moving said operator axially with respect to said gripper support, thereby to open and close said gripper jaws.

32. The apparatus as claimed in claim 31, wherein said means for moving said operator axially with respect to said gripper support includes an actuator connected between said operator and said gripper support.

33. The apparatus as claimed in claim 29, wherein said means for translating said carriage between said first and second positions includes:

a pair of spaced apart parallel rails supported between a pair of spaced apart rails supports, said carriage being slidingly on said rails; and, carriage actuator means for moving said carriage on said rails.

34. The apparatus as claimed in claim 33, wherein said carriage actuator means includes:
  a block slidingly mounted to said rails;
  a first actuator connected between said block and one of said rail supports; and,
  a second actuator connected between said carriage and said block.

35. The apparatus as claimed in claim 34, including:
  a stop positioned between said carriage and one of said rail supports; and,
  a stop positioned between said block and the other of said rail supports.

36. The apparatus as claimed in claim 35, wherein each of said stops includes a shock absorbing stop member adjustably attached to a rail support.

\* \* \* \* \*